United States Patent [19]

Micklus et al.

[11] 4,119,094
[45] Oct. 10, 1978

[54] COATED SUBSTRATE HAVING A LOW COEFFICIENT OF FRICTION HYDROPHILIC COATING AND A METHOD OF MAKING THE SAME

[75] Inventors: Michael J. Micklus, Somerville; David T. Ou-Yang, Raritan, both of N.J.

[73] Assignee: Biosearch Medical Products Inc., Raritan, N.J.

[21] Appl. No.: 889,249

[22] Filed: Mar. 23, 1978

Related U.S. Application Data

[62] Division of Ser. No. 822,412, Aug. 8, 1977, Pat. No. 4,100,309.

[51] Int. Cl.$^2$ .................. A61F 5/42; A61M 25/00
[52] U.S. Cl. .................. 128/132 R; 128/349 R; 128/294; 128/348; 3/1; 428/35; 428/36; 428/411; 428/420; 428/425; 428/480; 428/492; 428/521; 428/522; 260/859 R; 260/904
[58] Field of Search .................. 428/425, 35, 36, 411, 428/420, 522, 492, 521, 480; 206/69; 128/132 R, 294, 348, 349 R, 350 R, 351; 260/859 R, 77.5 CR; 3/1

[56] References Cited

U.S. PATENT DOCUMENTS

| 3,216,983 | 11/1965 | Shelanski | 260/77.5 CR |
|---|---|---|---|
| 3,336,918 | 8/1967 | Jeckel | 128/348 X |
| 3,787,525 | 1/1974 | McGarr | 260/859 R |
| 3,860,672 | 1/1975 | Lagally | 260/859 R |
| 3,939,049 | 2/1976 | Ratner | 260/859 R |
| 3,975,350 | 8/1976 | Hudgin | 128/348 |
| 3,987,497 | 10/1976 | Stoy | 3/1 |

OTHER PUBLICATIONS

"Transport Properties of Polyvinylpyrolidone–Polyisocyanate Interpolymer Membranes", R. L. Riley, et al., Gulf General Atomic, Oct. 15, 1969.

Primary Examiner—Ellis Robinson
Attorney, Agent, or Firm—Harding, Earley & Follmer

[57] ABSTRACT

A substrate is coated with a polyvinylpyrrolidone-polyurethane interpolymer. In the method, a polyisocyanate and a polyurethane in a solvent such as methyl ethyl ketone are applied to a substrate and the solvent evaporated. If the substrate is a polyurethane, only the polyisocyanate need be employed. Polyvinylpyrrolidone in a solvent is then applied to the treated substrate and the solvent evaporated. The invention is applied, for example, to a tube such as a catheter, a condom and a peristaltic pump tube.

11 Claims, 9 Drawing Figures

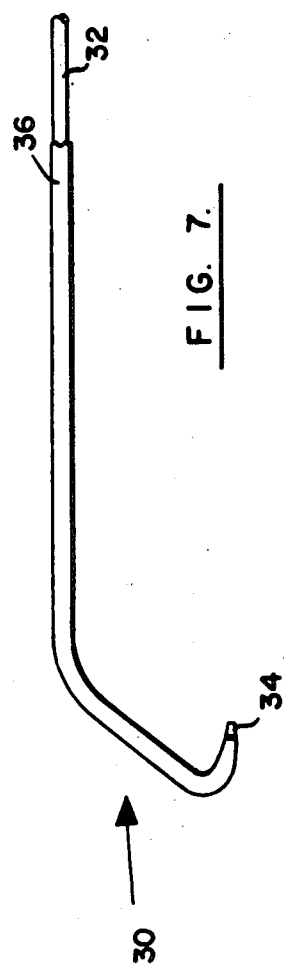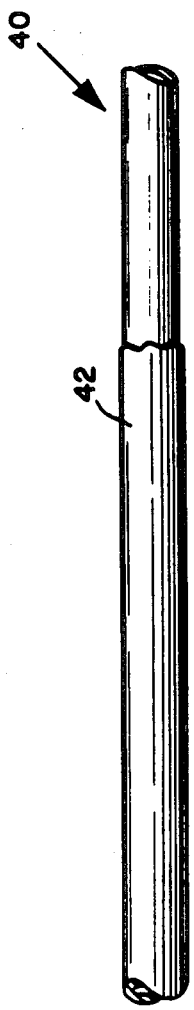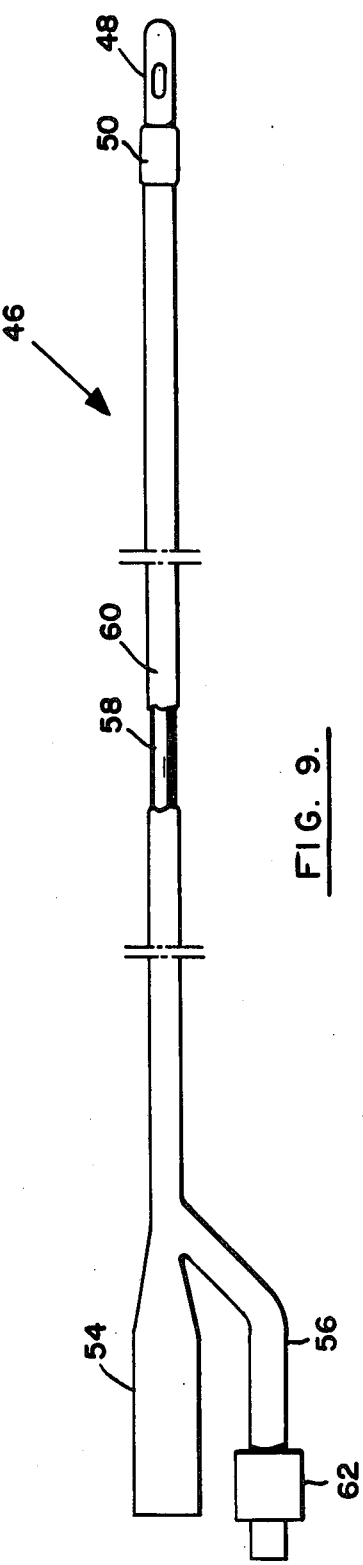

COATED SUBSTRATE HAVING A LOW COEFFICIENT OF FRICTION HYDROPHILIC COATING AND A METHOD OF MAKING THE SAME

This is a division of application Ser. No. 822,412, filed Aug. 8, 1977 now U.S. Pat. No. 4,100,309.

BACKGROUND OF THE INVENTION

For numerous applications such as contact lenses, catheters, peristaltic pump chambers, condoms, implant materials, arteriovenous shunts, gastroenteric feed tubes and endotracheal tubes it is desired to have a material such as a polyurethane, acrylic polyester, or a vinyl resin or a rubber having a much lower coefficient of friction when wet than is possible with those materials per se. In the prior art polyvinylpyrollidone has been chemically grafted to a polymer substrate by first activating the substrate by irradiation or chemically. The resultant coating does not have a very low coefficient of friction. Polyurethane coatings are well known, but do not have a very low coefficient of friction. Heretofore, polymer substrates have been given a lower coefficient of friction by coating them with a non-permanent coating such as silicone or given a fluorocarbon coating neither of which is hydrophilic and which do not have as low a coefficient of friction as desired. Also fluorocarbon coatings are hard to handle because they have a low coefficient of friction at all times.

These problems have been solved surprisingly by this invention by providing a coating of polyvinylpyrollidonepolyurethane interpolymer. The hydrophilic coatings of this invention are advantageous since they have a very low coefficient of friction when wetted with a water base liquid or a lower aliphatic alcohol such as methanol or ethanol and yet are much less slippery when dry. This is an advantage, for example, in the handling of catheters since it is desirable to have them not slippery for handling but protecting the patient by becoming slippery when contacting an aqueous fluid. This is an important advantage of the invention in view of the high degree of lubricity of the coatings. Further, the coating thickness is not limited to a few molecular monolayers as in the case of other methods such as chemical or radiation grafting and may be applied in thicknesses of several hundred micrometers. In addition the coatings are non-reactive with respect to living tissue and are non-thrombogenic when in contact with blood. For each of these reasons, the product and method of the invention are unique and of great value.

SUMMARY OF THE INVENTION

The invention comprises a substrate, for example a tube, coated with a polyvinylpyrollidone-polyurethane interpolymer and the method of making the same by applying a polyisocyanate and usually a polyurethane in a solvent and then applying a polyvinylpyrollidone in a solvent to form a polyvinylpyrollidonepolyurethane interpolymer.

THE INVENTION

The invention comprises a substrate coated with a polyvinylpyrollidone-polyurethane interpolymer. Any polyurethane may be used.

While the substrate may be any material to which conventional polyurethane coatings adhere, it is preferred to use polymer substrates such as a polyurethane resin, a vinyl resin such as polyvinylchloride, a polyacrylate such as polymethylmethacrylate, a polycarbonate, a polyester such as polyethylene terephthalate, polybutylene terephthalate, polytetramethylene terephthalate, or a rubber such as a latex rubber or polyisoprene.

The method of the invention comprises applying a polyisocyanate and a polyurethane in a solvent to the surface of the substrate to be coated with the interpolymer by dipping, spraying or the like and then evaporating the solvent preferably by air drying. This step forms a polyurethane coating with unreacted isocyanate groups on the substrate. Exemplary of the polyisocyanate are polymethylenepolyphenyl isocyanate, 4,4'-diphenylmethane diisocyanate and position isomers thereof, 2,4-tolylene diisocyanate and position isomers thereof, 3,4-dichlorophenyl diisocyanate and isoferrone isocyanate. Adducts or prepolymers of isocyanates and polyols such as the adduct of trimethylolpropane and diphenylmethane diisocyanate or tolylene diisocyanate are suitable. For further examples of polyisocyanates see *Encyclopedia of Polymer Science and Technology*, H. F. Mark, N. G. Gaylord and N. M. Bikales (eds.), (1969) incorporated herein by reference. Exemplary of the polyurethane is the reaction product of 2,4-tolylene diisocyanate and position isomers thereof, 4,4'-diphenylmethane diisocyanate and position isomers thereof, polymethylenepolyphenyl isocyanate, or 1,5-napthylene diisocyanate with 1,2-polypropylene glycol, polytetramethylene ether glycol, 1,4-butanediol, 1,4-butylene glycol, 1,3-butylene glycol, poly(1,4-oxybutylene) glycol, caprolactone, adipic acid esters, phthalic anhydride, ethylene glycol, 1,3-butylene glycol, 1,4-butylene glycol or diethylene glycol. (For further examples see *Encyclopedia of Polymer Science and Technology* cited above). Chain extenders with hydrogen-containing difunctional compounds such as water, diamines, or amino acids may be used. Chain extenders are exemplified by 1,4-butanediol, hexamethylene diamine, 4,4-methylene-bis(2-chloroaniline) (MOCA), trimethylolpropane, and ethanolamine. Other additives include accelerators, catalysts, stabilizers, plasticizers, or the like which improve or modify the properties of the urethane. Exemplary are dicumyl peroxide, benzothiazyldisulfide, mercapto benzothiazole, benzothiazole disulfide, polypropylene adipate, and metal salts such as potassium acetate, cobalt naphthenate, and zinc chloride.

The solvent is one which will not react with the isocyanate, i.e. it should be free of reactive amino, hydroxyl and carboxyl groups. Preferred solvents are dichloromethane, methyl ethyl ketone, acetone, ethyl lactate, chloroform, trichloroethylene and ethyl acetate. The hydroxyl of the ethyl lactate is not sufficiently reactive to be detrimental.

Preferred polyurethanes are polytetramethylene ether glycol-diphenylmethane diisocyanate (MDI), polytetramethylene ether glycol-tolylene diisocyanate (TDI), polytetramethylene ether glycol-isoferrone isocyanate, poly(1,4-oxybutylene) glycoldiphenylmethane diisocyanate (MDI), poly(1,4-oxybutylene) glycoltolylene diisocyanate (TDI), poly(1,4-oxybutylene) glycolisoferrone isocyanate, polyethylene glycol-diphenylmethane diisocyanate (MDI), polyethylene glycol-tolylene diisocyanate (TDI), polyethylene glycol-isoferrone isocyanate, polypropylene glycoldiphenylmethane diisocyanate (MDI), polypropylene glycol-tolylene diisocyanate (TDI), polypropylene glycol-isoferrone isocyanate, polycaprolactone-diphenylmethane diisocyanate (MDI), polycaprolactone-tolylene diisocyanate (TDI), polycaprolactoneisoferrone isocyanate, polyethylene adipate-diphenylmethane diisocyanate (MDI), polyethylene adipate-tolylene diisocyanate (TDI), polyethylene adipate-isoferrone isocyanate, polytetramethylene adipate-diphenylmethane diisocyanate (MDI), polytetramethylene adipate-tolylene diisocyanate (TDI), polytetramethylene adipate-isoferrone isocyanate, polyethylenepropylene adipate-diphenylmethane diisocyanate (MDI), polyethylene-propylene adipate-tolylene diisocyanate (TDI), and polyethylene-propylene adipate-isoferrone isocyanate polyurethanes.

Advantageously the polyisocyanate in the solution will be from about 0.4% to about 5% (weight to volume — W/V), preferably from about 0.4% to about 3% (W/V) and the polyurethane advantageously will be from about 0.3% to about 10% (weight to volume), preferably from about 0.3% to about 4% (W/V).

While the substrate generally need be in contact with the solution only briefly, for example 1 to 4 minutes, in the case of a rubber latex substrate a longer period of from about 15 to 120 minutes or more is desirable to achieve firm adherence of the final interpolymer coating to the rubber latex. Also with a rubber latex substrate a pretreatment step of soaking the rubber latex in a suitable solvent such as a chlorinated hydrocarbon solvent, for example, methylene chloride, chloroform, 1,1,1-trichloroethane, and ethylene chloride, for example from 15 to 120 minutes or more, to swell the rubber is advantageous.

The thus treated substrate is then coated with polyvinylpyrollidone in a solvent to form a polyvinylpyrollidonepolyurethane interpolymer. The polyvinylpyrollidone advantageously has an average molecular weight of at least 120,000 with the preferred average molecular weight being about 360,000. Exemplary of suitable solvents are chloroform, trichlorethylene, ethylene dichloride, methylene chloride and ethyl lactate. The solvent selected will be unreactive with the substrate. The polyvinylpyrollidone in the solution advantageously will be from about 0.5% to about 10% and preferably from about 1% to about 4% (weight to volume). While more than 10% of polyvinylpyrollidone can be used, no advantage is gained. The polyvinylpyrollidone in the solvent is applied by dipping, spraying or the like for a short period, for example from about 1 to 4 minutes. After the polyvinylpyrollidone solution has been applied to the coated substrate, the solvent is evaporated preferably by air drying. Advantageously the residual traces of solvent are removed by subjecting the coated substrate to a temperature of from about 50° to about 100° C., for example, in an oven. There remains a polyvinylpyrollidone-polyurethane interpolymer coating film on the substrate which when wet has an extremely low coefficient of friction and is hydrophilic.

If the substrate is of polyurethane, then the polyurethane in the solution may be eliminated and only the polyisocyanate need be used while carrying out the first step of the above described method.

All steps are carried out at room temperature except where otherwise specified.

The following Examples more specifically illustrate the invention:

EXAMPLE 1

(1) A clean rubber latex urinary catheter is placed in dichloromethane and allowed to swell for 1 hour.

(2) The catheter is removed from the dichloromethane and dipped immediately into a methyl ethyl ketone solution containing 2% (weight/volume) of equal weights of a 32% (weight/volume) solution of polycaprolactone-tolylene diisocyanate polyurethane in ethyl acetate (commercially available from Hughson Corporation as Chemlock 7000) and a 40% (weight/volume) solution of the adduct of trimethylolpropane-diphenylmethane diisocyanate in methyl ethyl ketone (Chemlock 7200). The catheter is allowed to remain in the solution for 1 hour.

(3) The catheter is removed and air dried for 3 minutes.

(4) Step 2 is repeated but only for 4 seconds.

(5) Step 3 is repeated.

(6) Steps 4 and 3 are repeated.

(7) The catheter is dipped into a 4% solution (weight to volume) of polyvinylpyrollidone (M.W. 360,000) dissolved in ethyl lactate for 5 seconds.

(8) The catheter is removed and air dried. The dry catheter is cured in an oven at 65° C. for 6 hours.

(9) The catheter is removed from the oven. All steps carried out at room temperature except where specifically stated otherwise.

EXAMPLE 2

(1) A peristaltic pump tube of polytetramethylene ether glycol-diphenylmethane diisocyanate (MDI)-polyurethane (available as Roylar E85 from Uniroyal Chemical, Division of Uniroyal, Inc., Naugatuck, Connecticut) is dipped into a 1% solution (weight/volume) of diphenylmethane diisocyanate (MDI), (available from Upjohn as Isonate 143 L) in methyl ethyl ketone for 1 minute.

(2) The polyurethane tubing is removed and air dried until the MEK solvent evaporates.

(3) The polyurethane tubing is dipped into a 3% (W/V) solution of polyvinylpyrollidone in chloroform for 1 minute.

(4) The tubing is air dried and then oven cured for 1 hour at 75° C. All steps carried out at room temperature unless specifically stated otherwise.

BRIEF DESCRIPTION OF THE DRAWINGS

FIG. 7 is a plan view of a cardiovascular catheter partially broken away;

FIG. 8 is a plan view of a peristaltic pump tube partially broken away; and

FIG. 9 is a plan view of a urethral catheter partially broken away.

DETAILED DESCRIPTION

Figure 1:
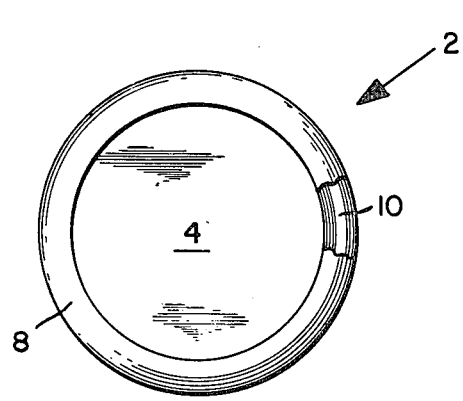
FIG. 1 is a plan view of a condom in accordance with the invention.
Figure 2:
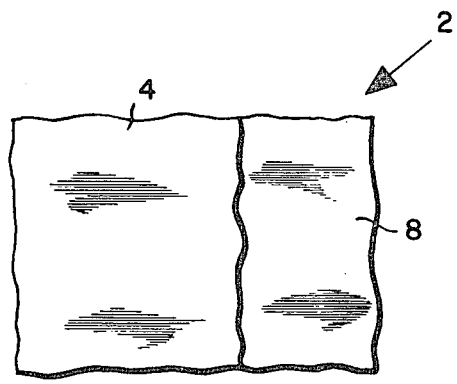
FIG. 2 is a fragmentary view of the condom of FIG. 1.
Figure 3:
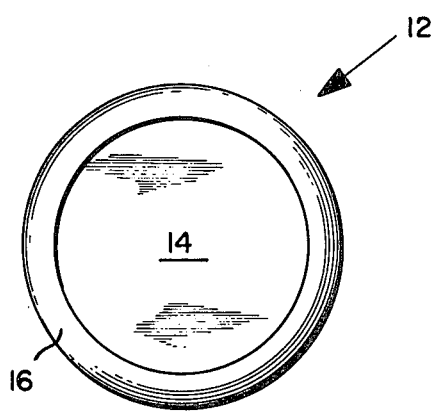
FIG. 3 is a modified condom in accordance with the invention.

A condom 2 in accordance with the invention is shown in FIG. 1. As best seen in FIG. 2, condom 2 has a base material or substrate 4 of polyisoprene the exterior of which is coated with a coating 8 of polyvinylpyrollidone-polyurethane interpolymer. The base material is secured to the conventional rubber band 10 at the inner end of condom 2.

Figure 4:
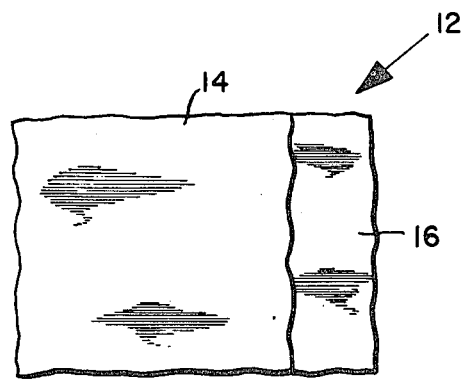
FIG. 4 is a fragmentary view of the condom of FIG. 3.

A condom 12 shown in FIG. 13 has, as best seen in FIG. 4, a base material or substrate 14 of polyurethane provided with an outer layer of polyvinylpyrollidone-polyurethane interpolymer 16.

Figure 5:
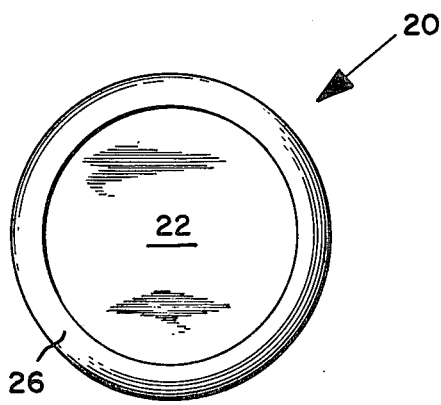
FIG. 5 is a modified condom in accordance with the invention.
Figure 6:
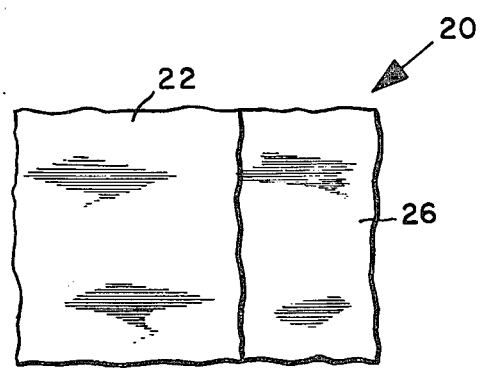
FIG. 6 is a fragmentary view of the condom of FIG. 5.

The condom 20 shown in FIG. 5 has, as best seen in FIG. 6, a base layer or substrate 22 of rubber latex to which is secured a film 26 of polyvinylpyrollidone-polyurethane interpolymer.

As shown in FIG. 7, a cardiovascular catheter 30 is formed from a tubular member 32 of polyvinylchloride having a reduced tip end 34 coated with a layer 36 of polyvinylpyrollidone interpolymer.

As shown in FIG. 8 a peristaltic pump tube 40 of polyvinylchloride is coated with a layer 42 of polyvinylpyrollidone-polyurethane interpolymer.

As shown in FIG. 9, a urethral catheter 46 has a tip 48, a balloon portion 50, a drain connector 54 and a valve branch 56 formed from a branched tube 58 of rubber latex coated with a polyvinylpyrollidone-polyurethane interpolymer 60. An inflation valve 62 is secured to valve branch 56.

It will be understood that the above described embodiments are illustrative and are not intended to be limiting.

We claim:

1. An article having a very low coefficient of friction when wetting with a water base liquid or a lower aliphatic alcohol comprising:
   a substrate to which conventional polyurethanes adhere, and
   a cured polyvinylpyrollidone-polyurethane interpolymer coating on said substrate.

2. An article in accordance with claim 1 in which the substrate is of polyurethane.

3. An article in accordance with claim 1 in which the substrate is of a material other than polyurethane coated with a film of polyurethane.

4. An article in accordance with claim 1 having a polyvinylchloride substrate.

5. An article in accordance with claim 1 having a rubber latex substrate.

6. An article in accordance with claim 1 having a polyisoprene substrate.

7. An article in accordance with claim 1 having a polyester resin substrate.

8. A condom having a base material of polyurethane, and
   a cured coating of a polyvinylpyrollidone-polyurethane interpolymer on the outside of said base material wherein said coated condom has a very low coefficient of friction when wetted with a water base liquid or a lower aliphatic alcohol.

9. A resilient tube which conventional polyurethanes adhere coated with a cured polyvinylpyrollidonepolyurethane interpolymer to provide the tube with a surface having a very low coefficient of friction when wetted with a water base liquid.

10. A device in accordance with claim 9 in which the tube is of rubber latex.

11. A catheter having a tubular body which conventional polyurethanes adhere, and a cured coating of polyvinylpyrollidone-polyurethane interpolymer on the outside of said body providing the outer surface of said body with a coating having a very low coefficient of friction when wetted with a water base liquid or a lower aliphatic alcohol.

* * * * *

UNITED STATES PATENT OFFICE
CERTIFICATE OF CORRECTION

Patent No. 4,119,094                 Dated October 10, 1978

Inventor(s) Michael J. Micklus et al.

It is certified that error appears in the above-identified patent and that said Letters Patent are hereby corrected as shown below:

In column 5, line 30 (claim 1), substitute --wetted-- for "wetting". In column 6, line 21 (claim 9) insert --to-- before "which". In line 28 (claim 11), insert --to-- before "which".

Signed and Sealed this

Sixteenth Day of January 1979

[SEAL]

Attest:

RUTH C. MASON  
Attesting Officer

DONALD W. BANNER  
Commissioner of Patents and Trademarks